US009759222B2

(12) United States Patent  
Zimmermann et al.

(10) Patent No.: US 9,759,222 B2  
(45) Date of Patent: Sep. 12, 2017

(54) BLOOD PUMP ROTOR BEARINGS

(71) Applicant: Thoratec Corporation, Pleasanton, CA (US)

(72) Inventors: Stephen Zimmermann, Fremont, CA (US); Carine Hoarau, Lafayette, CA (US); John Duc Nguyen, San Ramon, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 14/835,572

(22) Filed: Aug. 25, 2015

(65) Prior Publication Data

US 2015/0361988 A1 Dec. 17, 2015

Related U.S. Application Data

(63) Continuation of application No. 13/804,983, filed on Mar. 14, 2013, now Pat. No. 9,144,638.

(51) Int. Cl.
*F16C 33/32* (2006.01)
*F16C 33/38* (2006.01)
(Continued)

(52) U.S. Cl.
CPC .......... *F04D 29/049* (2013.01); *A61M 1/1013* (2014.02); *A61M 1/122* (2014.02); *C23C 16/44* (2013.01); *F04D 1/00* (2013.01); *F04D 29/22* (2013.01); *F16C 17/04* (2013.01); *F16C 33/32* (2013.01); *F16C 33/3831* (2013.01);
(Continued)

(58) Field of Classification Search
CPC ...... F16C 17/04; F16C 33/32; F16C 33/3831; F16C 2316/18; F16C 41/005; F04D 29/049; F04D 1/00; F04D 29/22; F04D 13/02; A61M 1/1013; A61M 1/122; A61M 1/101; A61M 2207/00; C23C 16/44; Y10T 29/49657
USPC ........ 384/108, 110, 206, 245–247, 261, 369, 384/371; 415/104, 132, 206, 229, 900; 600/14, 16–18; 417/355, 413.1, 420, 417/423; 623/3.1, 3.26; 29/898.048, 29/898.13
See application file for complete search history.

(56) References Cited

U.S. PATENT DOCUMENTS 2,321,448 A 6/1943 Anderson et al.
2,369,500 A 2/1945 Wacber
(Continued)

FOREIGN PATENT DOCUMENTS

DE 102012202411 8/2013
EP 1019635 7/2000
(Continued)

*Primary Examiner* — Marcus Charles
(74) *Attorney, Agent, or Firm* — Kilpatrick Townsend & Stockton LLP

(57) ABSTRACT

A bearing assembly for use in a blood pump includes a first component that has a convex bearing surface and a first outer surface proximate the convex bearing surface. The bearing assembly includes a second component that a concave bearing surface and a second outer surface proximate the concave bearing surface, the concave bearing surface being configured to receive the convex bearing surface. A plurality of grooves are defined through the convex bearing surface and first outer surface or through the concave bearing surface and the second outer surface.

24 Claims, 8 Drawing Sheets

(51) Int. Cl.
*A61M 1/10* (2006.01)
*F16C 17/04* (2006.01)
*F04D 29/049* (2006.01)
*F04D 29/22* (2006.01)
*C23C 16/44* (2006.01)
*F04D 1/00* (2006.01)
*F16C 33/64* (2006.01)
*F16C 41/00* (2006.01)
*A61M 1/12* (2006.01)

(52) U.S. Cl.
CPC .......... *F16C 41/005* (2013.01); *A61M 1/101* (2013.01); *A61M 1/1017* (2014.02); *A61M 2207/00* (2013.01); *F16C 2316/18* (2013.01); *Y10T 29/49657* (2015.01)

(56) References Cited

U.S. PATENT DOCUMENTS

| | | |
|---|---|---|
| 2,653,456 A | 9/1953 | Heym et al. |
| 2,926,975 A | 3/1960 | Karde et al. |
| 4,036,032 A | 7/1977 | Durum |
| 4,141,603 A | 2/1979 | Remmers et al. |
| 4,238,936 A | 12/1980 | Devos |
| 4,473,360 A | 9/1984 | Devos |
| 4,573,810 A | 3/1986 | Fust et al. |
| 4,625,712 A | 12/1986 | Wampler |
| 4,678,348 A | 7/1987 | Tielemans et al. |
| 4,704,121 A | 11/1987 | Moise et al. |
| 4,730,989 A | 3/1988 | Laing |
| 5,167,584 A | 12/1992 | Krude et al. |
| 5,211,546 A | 5/1993 | Isaacson et al. |
| 5,360,445 A * | 11/1994 | Goldowsky ........... A61M 1/106 600/16 |
| 5,385,454 A | 1/1995 | Kobayashi et al. |
| 5,393,207 A | 2/1995 | Maher et al. |
| 5,588,812 A | 12/1996 | Taylor et al. |
| 5,707,218 A | 1/1998 | Maher et al. |
| 5,722,775 A | 3/1998 | Thijsse et al. |
| 5,951,263 A | 9/1999 | Taylor et al. |
| 6,018,208 A | 1/2000 | Maher et al. |
| 6,093,001 A * | 7/2000 | Burgreen ............ A61M 1/101 415/176 |
| 6,109,900 A | 8/2000 | Ishizuka et al. |
| 6,120,537 A * | 9/2000 | Wampler ............ A61M 1/101 415/229 |
| 6,123,659 A | 9/2000 | le Blanc et al. |
| 6,127,756 A | 10/2000 | Iwaki et al. |
| 6,135,710 A | 10/2000 | Araki et al. |
| 6,146,281 A | 11/2000 | Iijima et al. |
| 6,186,665 B1 | 2/2001 | Maher et al. |
| 6,196,722 B1 | 3/2001 | Saito et al. |
| 6,302,549 B1 | 10/2001 | Branham et al. |
| 6,722,863 B2 | 4/2004 | Maeda et al. |
| 7,682,301 B2 | 3/2010 | Wampler et al. |
| 7,699,529 B2 | 4/2010 | Engesser et al. |
| 7,753,645 B2 | 7/2010 | Wampler et al. |
| 7,762,941 B2 | 7/2010 | Jarvik et al. |
| 7,798,952 B2 | 9/2010 | Tansley et al. |
| 7,802,966 B2 | 9/2010 | Wampler et al. |
| 7,841,976 B2 | 11/2010 | McBride et al. |
| 7,862,501 B2 | 1/2011 | Woodard |
| 7,927,068 B2 | 4/2011 | McBride et al. |
| 7,959,551 B2 | 6/2011 | Jarvik |
| 7,976,271 B2 | 7/2011 | LaRose et al. |
| 7,988,728 B2 | 8/2011 | Ayre |
| 8,002,518 B2 | 8/2011 | Woodard et al. |
| 8,007,254 B2 | 8/2011 | Marquis et al. |
| 8,088,059 B2 | 1/2012 | Jarvik et al. |
| 8,118,724 B2 | 2/2012 | Wampler et al. |
| 8,282,359 B2 | 10/2012 | Ayre et al. |
| 8,353,686 B2 | 1/2013 | Cook |
| 8,366,381 B2 | 2/2013 | Woodard et al. |
| 8,366,599 B2 | 2/2013 | Tansley et al. |
| 8,376,707 B2 | 2/2013 | McBride et al. |
| 2005/0124421 A1 | 6/2005 | Park |
| 2005/0135948 A1 * | 6/2005 | Olsen .................. F16C 32/0448 417/423.12 |
| 2007/0231135 A1 * | 10/2007 | Wampler ............. A61M 1/101 415/229 |
| 2008/0262289 A1 * | 10/2008 | Goldowsky ........... A61M 1/101 600/16 |
| 2008/0269880 A1 | 10/2008 | Jarvik |
| 2011/0004046 A1 | 1/2011 | Campbell et al. |
| 2011/0065978 A1 | 3/2011 | Tansley et al. |
| 2011/0071338 A1 | 3/2011 | McBride et al. |
| 2011/0160516 A1 | 6/2011 | Dague et al. |
| 2011/0236210 A1 | 9/2011 | McBride et al. |
| 2011/0238172 A1 * | 9/2011 | Akdis .................. A61M 1/101 623/3.11 |
| 2011/0243759 A1 * | 10/2011 | Ozaki .................. A61M 1/101 417/279 |
| 2012/0004497 A1 | 1/2012 | Ayre et al. |
| 2012/0016178 A1 | 1/2012 | Woodard et al. |
| 2012/0095281 A1 | 4/2012 | Reichenbach et al. |
| 2013/0052038 A1 | 2/2013 | Ayre et al. |
| 2013/0317283 A1 | 11/2013 | LaRose et al. |
| 2014/0275722 A1 | 9/2014 | Zimmermann et al. |
| 2015/0335803 A1 * | 11/2015 | Yamane .................... F04D 3/00 600/16 |

FOREIGN PATENT DOCUMENTS

| | | | |
|---|---|---|---|
| EP | 2554191 | 2/2013 | |
| FR | 2608702 | 6/1988 | |
| JP | EP-1598087 A2 * | 11/2005 | ............ A61M 1/101 |
| JP | 2013212218 A * | 1/2013 | ............ F04D 13/02 |
| JP | 2013099536 | 5/2013 | |
| WO | 0043054 | 7/2000 | |
| WO | 2004101029 | 11/2004 | |
| WO | 2009010888 | 1/2009 | |
| WO | 2012051454 | 4/2012 | |

* cited by examiner

BLOOD PUMP ROTOR BEARINGS

CROSS-REFERENCES TO RELATED APPLICATIONS

This application is a continuation application of U.S. application Ser. No. 13/804,983, filed Mar. 14, 2013, and titled "Blood Pump Rotor Bearings," the entire contents of which are incorporated herein by reference in its entirety.

TECHNICAL FIELD

This invention relates to blood pump rotor bearings.

BACKGROUND

Heart assist devices or pumps can be connected in the circulatory system to pump blood from one location of the vasculature to another. A common approach is to pump blood from either ventricle or atrium of a heart to the ascending aorta. A pump supplementing or replacing a ventricle is known as a ventricular assist device, or VAD. A VAD is useful when the ventricle alone is incapable of providing adequate blood flow. Rotary pumps typically include a rotor that rotates within a housing. The rotor may be rotatably supported within the housing by bearings at the fore and/or aft ends of the pump.

SUMMARY

In some implementations, a bearing assembly for use in a blood pump includes a first component having a convex bearing surface and a first outer surface proximate the convex bearing surface. The bearing assembly includes a second component that has a concave bearing surface and a second outer surface proximate the concave bearing surface. The concave bearing surface is configured to receive the convex bearing surface. Multiple grooves are defined through the convex bearing surface and first outer surface or through the concave bearing surface and the second outer surface.

Implementations may include one or more of the following features. At least one of the convex bearing surface and the concave bearing surface is hemispherical, frustoconical, or parabolic. The first component and the second components are configured to maintain a gap between the first and second bearing surfaces. The gap is sized to allow blood flow. The first component defines a plurality of grooves in the convex bearing surface and/or the second component defines a plurality of grooves in the concave bearing component. Each of the plurality of grooves has a depth of varies along its length. A majority of at least one of the first and second bearing surfaces defines a portion of the plurality of grooves. At least one of the first and second outer surfaces is cylindrical. The first outer surface has a curvature that is different from a curvature of the second outer surface. The bearing assembly has an axis of rotation, the first component has one or more generally planar sidewalls that extend parallel to the axis of rotation, the sidewalls forming an edge with the convex bearing surface. The first component defines channels in the exterior of the first component, the channels extending along the axis of rotation, the channels extending from the bearing surface to a side surface extending circumferentially about the axis of rotation. One or more of the bearing components define longitudinal channels, and the longitudinal channels are defined radially inward toward the axis of rotation. The concave bearing surface or the convex bearing surface includes a plurality of surface segments separated by recesses spaced apart about the axis of rotation. The channels are straight, and each channel is defined along a plane that intersects the axis of rotation. The channels are offset from the axis of rotation. The grooves defined in one of the components extend along the axis of rotation beyond the longitudinal extent of the other bearing component.

In another general aspect, a component of a bearing assembly for use in a blood pump includes a first component having a concave bearing surface and an outer surface proximate the concave bearing surface, the outer surface extending at least partially about the concave bearing surface. The first component is configured to rotatably couple to a second component along an axis of rotation. The first component defines a plurality of bores that extend from the outer surface toward the axis of rotation, the bores establishing fluid communication between the outer surface and the concave bearing surface.

Implementations may include one or more of the following features. For example, the concave bearing surface is located in a hemispherical, frustoconical, or parabolic recess. The outer surface is cylindrical. A center portion of the concave bearing surface defines a central chamber in fluid communication with the concave bearing surface. The bores extend through the first component from the outer surface to the central chamber. The outer surface is cylindrical, and the bores are equally spaced apart about the axis of rotation. Each of the plurality of bores extends inward toward the axis of rotation along a direction that is substantially orthogonal to the axis of rotation. Each of the plurality of bores extends inward toward the axis of rotation along a direction that is diagonal to the axis of rotation. Each of the plurality of bores extends along a linear trajectory and has a cross-sectional diameter that is substantially constant along the extent of the bore.

In another general aspect, a blood pump includes a housing, a rotor disposed within the housing and having an axis of rotation, and a mechanical bearing supporting the rotor. The mechanical bearing is configured to be lubricated by blood during operation of the blood pump. The mechanical bearing includes a first component having a convex bearing surface and a first outer surface proximate the convex bearing surface. The mechanical bearing also includes a second component having a concave bearing surface and a second outer surface proximate the concave bearing surface. The concave bearing surface is configured to receive the convex bearing surface. A plurality of voids are defined through the convex bearing surface and first outer surface or through the concave bearing surface and the second outer surface. In some implementations, the voids are in the form of grooves or bores.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference symbols in the various drawings indicate like elements.

DETAILED DESCRIPTION

Figure 1:
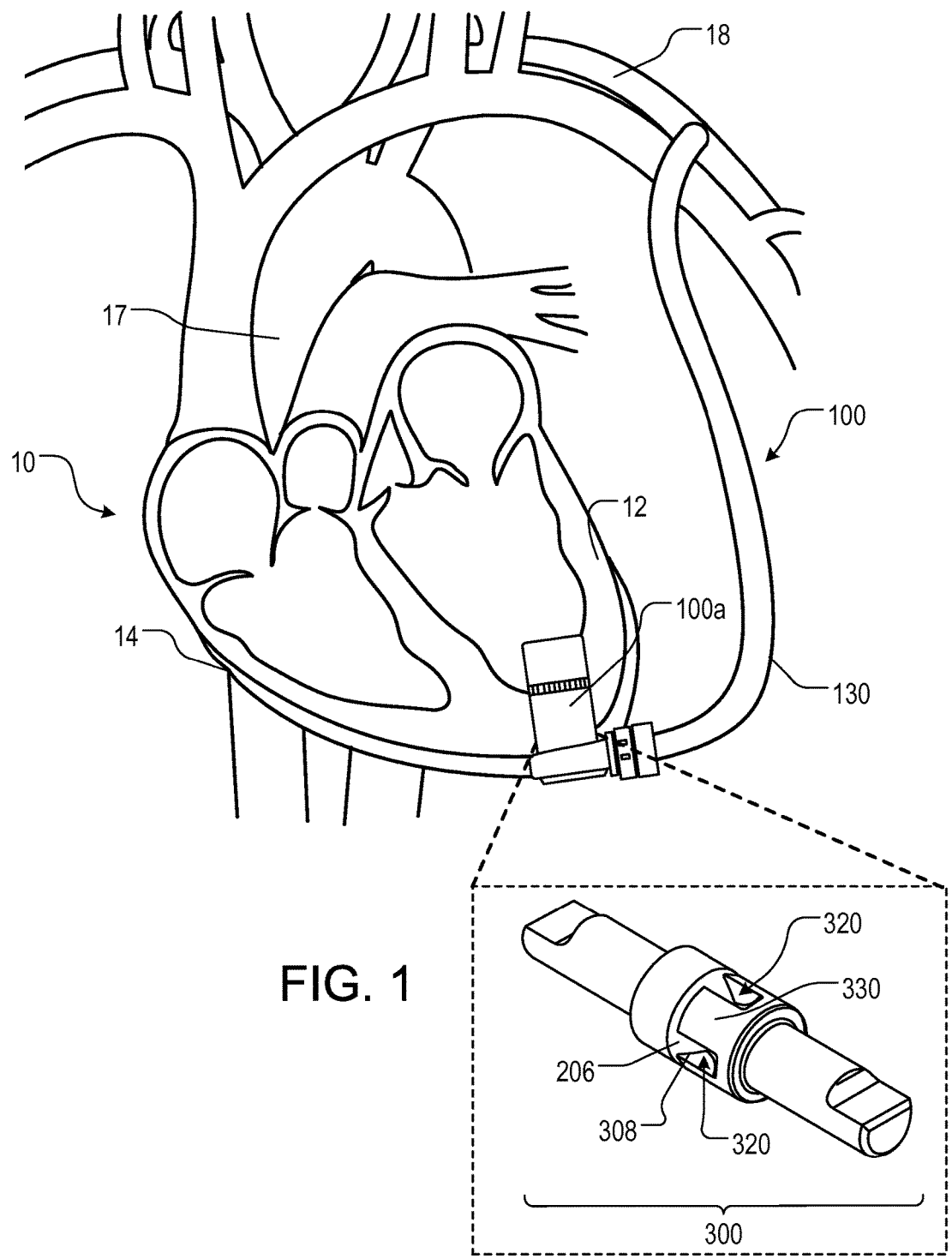
FIG. 1 is a diagram of a blood pump assembly connected to a heart of a patient requiring treatment.

Referring to FIG. 1, a blood pump assembly 100 can be implanted in a patient's body to supplement, or in some cases replace, the natural pumping function of a heart 10. Aspects of the pump assembly 100 are similar to those disclosed in U.S. Pat. No. 5,951,263, U.S. Pat. No. 6,186,665, U.S. application Ser. No. 13/273,185 filed Oct. 13, 2011 and entitled PUMPING BLOOD, and U.S. application Ser. No. 12/394,244 filed Feb. 27, 2009 and entitled BLOOD FLOW METER, the entire contents of which patents and applications are incorporated herein by reference for all purposes. The blood pump assembly 100 includes a blood pump 100a, which can be implanted to receive blood from the heart 10, for example, from a left ventricle 12 of the heart 10. As shown, the blood pump 100a pumps blood through an outflow conduit 130 to the patient's circulatory system, for example, to an aorta 17 or a peripheral artery 18. The blood pump assembly 100 can also be implanted such that the blood pump 100a receives blood from a right ventricle 14 of the heart 10 and supplies blood to, for example, a pulmonary artery.

As discussed further below, the pump 100a includes one or more mechanical, bloodimmersed bearings, such as the bearing assembly 300 illustrated. The bearing assembly 300 includes bearing surfaces 206, 308 that are lubricated by a fluid (e.g., blood) and act against each other to stabilize a rotor within the pump 100a. Pump 100a includes features to enhance or modify the flow of fluid through the bearings. The exemplary bearing surface 308 includes voids 320, such as grooves, channels, recesses, or gaps. In some implementations, the opposing bearing surface 206 defines voids in addition to or instead of the bearing surface 308. In some implementations, both bearing surface 308 and opposing bearing surface 206 define voids. The bearing surface 308 and opposing bearing surface 206 may be dimensioned and configured to cooperate with each other. For example, a flow enhancing feature may be formed by the mating of the surface 308 and surface 206.

The exemplary voids 320 may serve several purposes. The voids may reduce the amount of bearing surface area that acts against an opposing bearing surface, reducing friction and thereby increasing the power efficiency of the pump 100a. In addition, the voids 320 may act to increase the amount of surface area of the bearing assembly 300 that is exposed to blood, which can promote dissipation of heat from the bearing assembly 300. The voids can also be configured to provide a flow channel through the bearings for washing of the bearings. Washing the bearings can provide a cooling effect. It can also serve to wash away particulates, for example, particulates caused by rubbing of the bearing surfaces against each other. Over time, these particulates can accumulate and increase the risk of thrombus formation.

The exemplary voids 320 extend beyond the bearing surfaces 308 to an outer surface 330 that is exposed to the flow of blood within the pump 100a. As a result, the voids 320 can provide a passage for blood flow to enter a gap between the bearing surfaces 206, 308, improving lubrication at the bearing surfaces 206, 308. In addition, blood flowing through the voids 320 can wash the bearing interface and expel particles within the bearing assembly 300.

Figure 2:
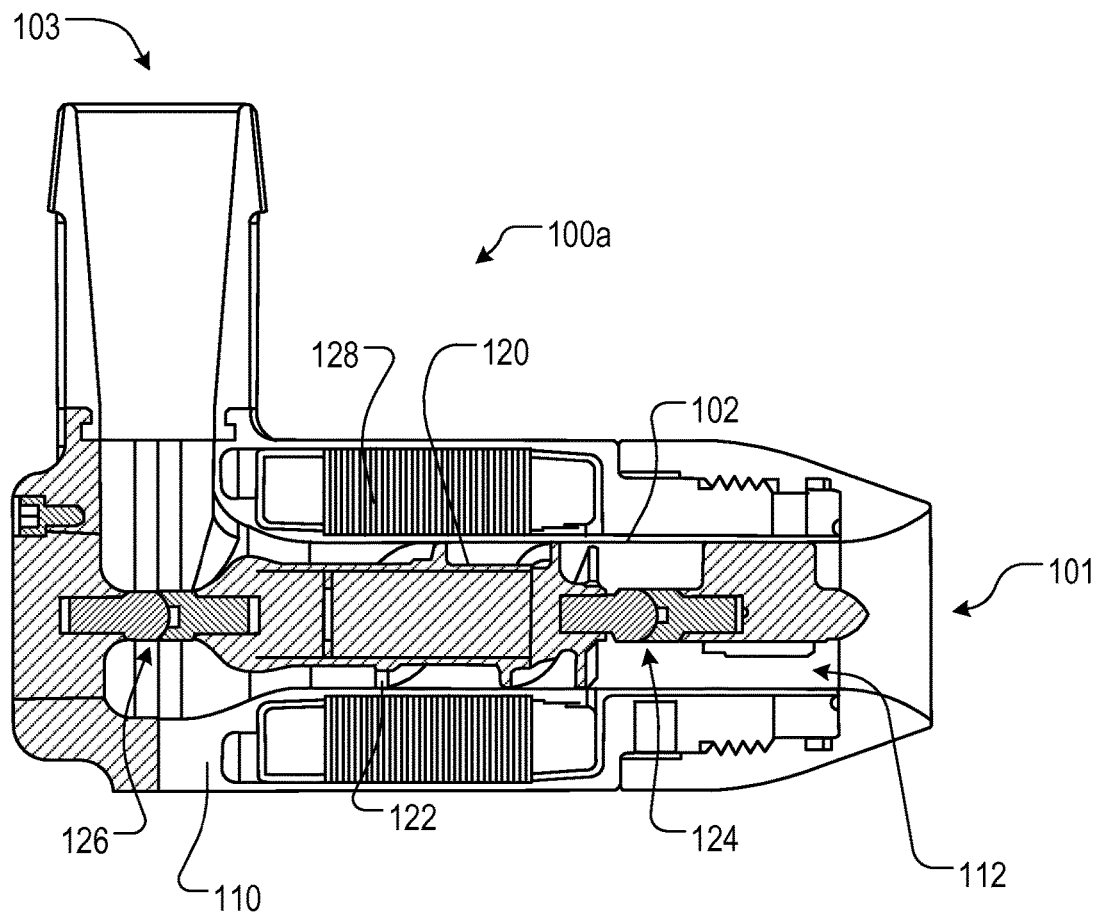
FIG. 2 is a cross-sectional view of a blood pump of the blood pump assembly of FIG. 1.

Referring to FIG. 2, the blood pump 100a includes a housing 110 that defines a blood flow path 112. Blood enters the housing 110 through an inlet 101, passes through a central tubular region 102 of the housing 110, and exits through an outlet 103. The housing 110 contains a motor stator 128, which drives rotation of a rotor 120 located in the blood flow path 112. As the rotor 120 rotates, blades 122 on the rotor 120 impart energy to the blood flow, resulting in pressure and blood flow at the outlet 103.

The rotor 120 is suspended in the housing 110 by fore and aft mechanical, bloodimmersed bearings 124, 126 that limit axial translation of the rotor 120. The bearings 124, 126 also limit the rotor from shifting off its axis of rotation. Any of the various bearing assemblies described below can be used as either or both of the bearings 124, 126. In some implementations, the two bearings 124, 126 have differing sizes, types, or configurations. The blood pump 100a can include additional features as described in U.S. Patent Application Publication No. 2012/0095281, which is incorporated by reference herein in its entirety.

Figure 3A:
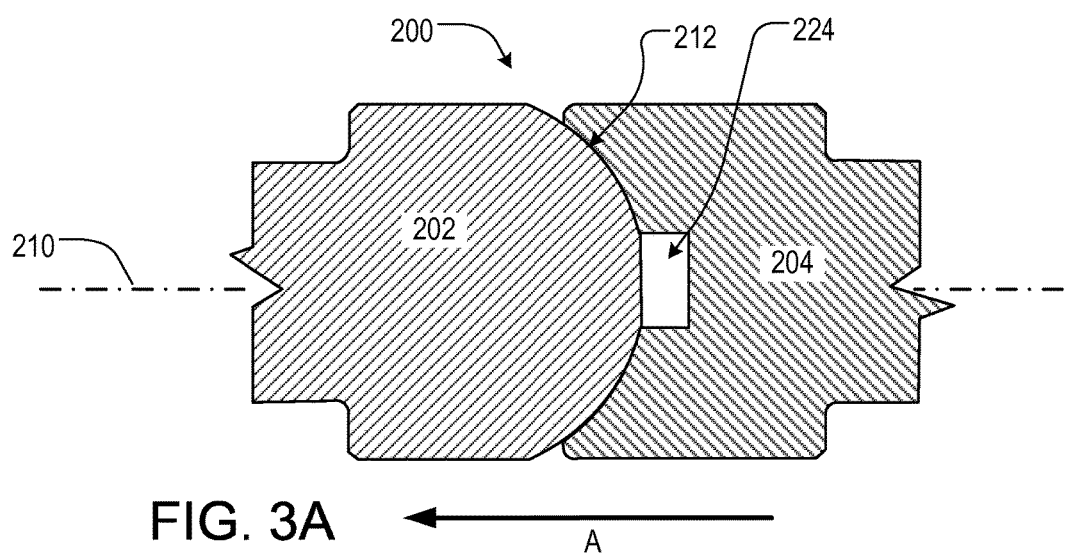
FIG. 3A is a cross-sectional view of a bearing of the blood pump of FIG. 2.
Figures 3B, 3C:
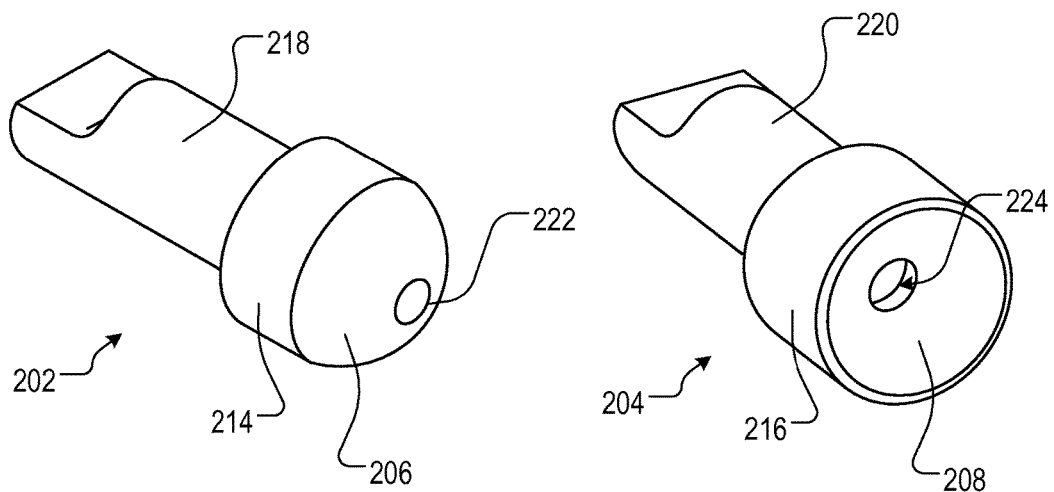
FIGS. 3B and 3C are perspective views of components of the bearings of FIG. 3A.

Referring to FIGS. 3A-3C, an example bearing assembly 200 illustrates general aspects of bearing assemblies that can be used with the pump 100a. The bearing assembly 300 shown in FIG. 1 and other bearing assemblies described below include features of the bearing assembly 200 and additionally define voids through one or more components of the bearing assembly 200.

The bearing assembly 200 has an axis of rotation 210 (e.g., a central longitudinal axis) that coincides with the axis of rotation of the rotor 120. The bearing assembly 200 includes a ball component 202 and a socket component 204. Components 202, 204 include respective bearing surfaces 206, 208 that act against each other to stabilize the rotor 120 in the axial and radial directions. The bearing surfaces 206, 208 interact with each other to maintain, for example, the longitudinal position of the rotor 120 along the axis 210 and/or the position of the rotor 120 centered on the axis 210. In some implementations, the bearing surfaces 206, 208 are located opposite each other and face toward each other along the axis of rotation 310. The bearing surfaces 206, 208 may contact each other during operation, however the bearing surfaces are typically separated by a gap filled with a lubricant, in this instance, blood. Thus the bearing surfaces 206, 208 may act against each other through a lubricant to stabilize the rotor 120 without direct or continued contact. In some implementations, the bearing surface of a component is a surface located closest to the opposing bearing component.

Referring to FIG. 3B, the ball component 202 includes a generally convex bearing surface 206 and an outer surface 214. The convex bearing surface 206 is located at an end of the ball component 202, and is centered about the axis 210. The bearing surface 206 of the ball component 202 may be generally hemispherical, frustoconical, or parabolic. In some implementations, a center portion of the bearing surface 206 includes a flat surface 222 oriented generally perpendicular to the central axis 210. The outer surface 214 is located proximate the convex bearing surface 206, for example, adjacent to the convex bearing surface 206. In some implementations, the outer surface 214 is cylindrical or frustoconical, and may be centered about the axis 210.

Referring to FIG. 3C, the socket component 204 includes a generally concave bearing surface 208 that is complementary to the convex bearing surface 206. The bearing surface 208 of the socket component 204 may define a generally hemispherical, frustoconical, or parabolic recess in which to receive the convex bearing surface 206 of the ball component 202. In some implementations, a center portion of the concave bearing surface 208 defines a chamber 224, which may be cylindrical in shape and may be located at the center of the concave bearing surface 206.

The socket component 204 also includes an outer surface 216 proximate the bearing surface 208. The outer surface 216 adjoins the bearing surface 208, for example, located about the concave bearing surface 208 and extending beyond an axial extent of the bearing surface 208. In some implementations, the outer surface 216 is cylindrical or frustoconical, and may be centered about the axis 210.

The bearing components 202, 204 can be formed of various biocompatible materials, for example, ceramic, stone (e.g., a sapphire, a ruby, or another crystal), or metal. The bearing assembly 200 can be mounted within a pump, such as the pump 100a (FIG. 2), via mounting shafts 218, 220 that extend longitudinally from the ball and socket components 10 202, 204, respectively.

Referring again to FIG. 3A, in use, the components 202, 204 rotatably engage each other along the axis of rotation 210. One of the components 202, 204 is coupled to the housing 110 of the pump 100a, and the other component 202, 204 is coupled to the rotor 120. The components 202, 204 are arranged to produce a precise bearing gap 212 between the bearing surfaces 206, 208. In a fluid environment, such as blood, the gap 212 can be maintained to be between about 0.0001 inches to about 0.0006 inches. In some implementations, the gap 212 can be approximately 0.0002 inches.

During operation of the blood pump 100a, blood travelling through the pump 100a flows past the bearings 124, 126. As shown in FIG. 3A, in the example illustrated, each of the bearings 124, 126 is arranged in the pump 100a so that blood flows over the socket component 204 before reaching the ball component 202. Alternatively, positions of the socket component 204 and ball component may be reversed such that blood first flows over the ball component 202 before reaching the socket component 204.

When blood flows past the bearing assembly 200 in the direction indicated by arrow A, blood fills the bearing gap 212 and lubricates the interface of the components 202, 204. As a result, the bearing surfaces 206, 208 generally do not contact each other while the rotor 120 is rotating, because they are separated by a thin layer of blood. Blood can flow over and around the bearing components 202, 204 and through the bearing gap 212. This flow can dissipate heat to cool the bearing assembly 200, can decrease friction at the bearing interface, and can limit the potential for thrombus and other occlusions. In some instances, obstructions in a bearing assembly may cause power spikes or pump stoppage. Increasing blood flow through the bearing gap 212 may reduce the risk of power spikes or pump stoppage due to bearing malfunction.

In the bearing assembly 200 shown in FIG. 3A, the bearing surfaces 206, 208 are generally smooth and continuous. As a result, the bearing gap 212 between the load bearing surfaces is generally uniform and continuous during operation of the blood pump 100a. In some implementations, as described further below, one or both bearing surfaces may be discontinuous. Separation of the bearing components by the bearing gap distance may occur only at discontinuous portions of the bearing surfaces, while recessed surfaces located between segments of the bearing surfaces are spaced apart by more than the bearing gap.

Figure 4:
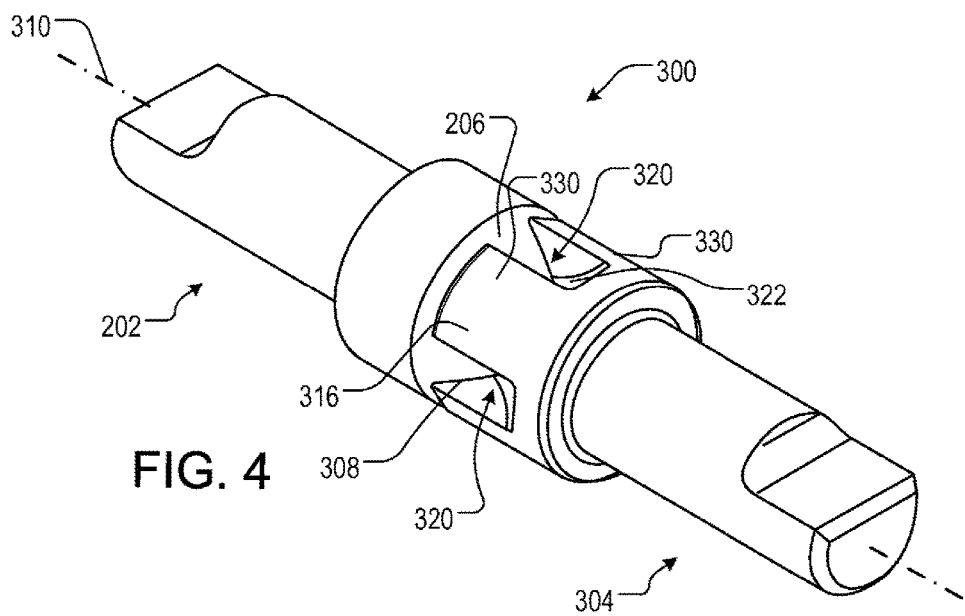
FIGS. 4-8 are perspective views of alternative bearings.

Referring to FIG. 4, the bearing assembly 300, which was shown in FIG. 1, includes the ball component 202 and a socket component 304. The socket component 304 defines grooves 320 or other voids that can help contribute to, for example, improving heat dissipation, decreasing overall surface contact at the bearing interface, reducing thrombus and other occlusions, and reducing the risk of power spikes or pump stoppage due to bearing malfunction. The bearing assembly 300 permits rotation about a central axis 310.

The socket component 304 includes a concave bearing surface 308 that is proximate and adjoined to an outer surface 316. In contrast to the concave bearing surface 208 (FIG. 3C), which is generally smooth and continuous, the bearing surface 308 is discontinuous due to the grooves 320. The grooves 320 can be in the form of grooves or cutouts that extend through the socket component 304, for example, from the outer surface 316 to the concave bearing surface 308. The grooves 320 also extend along the direction of the axis 304 to the end of the socket component 304. The socket component 304 has multiple projections 330 that extend along the axis 310 and have free ends. The projections 330 are separated by the grooves 320. The concave bearing surface 308 is formed at least partially by discontinuous inner regions of the projections 330.

The surface area of the concave bearing surface 308, which acts against the convex bearing surface 206 of the ball component 202, is lower than the surface area of the concave bearing surface 208. Because the concave bearing surface 308 has a lower surface area, the socket component 304 can cause lower friction and energy loss in the pump compared to the socket component 204, while providing substantially the same amount of stabilization to the rotor 120.

Like the convex bearing surface 308, the outer surface 316 is discontinuous and defines portions of the grooves 320. That is, the continuity of the bearing and outer surfaces 308, 316 in a circumferential direction about the axis 310 is broken by the presence of grooves 320.

The voids can be formed by various techniques. For example, the voids can be formed by removing material (e.g., milling or etching) from the respective bearing component or depositing material (e.g., vapor deposition). The component can also be formed with voids in a single step, such as by molding. The component can also be formed by other techniques as would be understood by one of skill in the art from the foregoing.

The grooves 320 are generally open channels that allow the passage of blood. The exemplary grooves have smooth, rounded sidewalls. During pump operation, blood can flow into the groove 320 by entering through an opening defined by the outer surface 316 and can exit the groove 320 through an opening defined by the bearing surface 308. Alternatively, or additionally, blood may enter the groove 320 through the opening in the bearing surface 308 while exiting through the opening in the outer surface 316. The resulting increased blood flow into the interface between the components 202, 304 can lead to, for example, increased cooling of the bearing assembly 300. Additionally, the grooves 320 can provide a passageway through which particles that may have formed or become dislodged in the bearing interface may be jettisoned.

Each groove 320 can have a bottom surface 322 that faces outward through the open portion of the groove 320. In some implementations, the bottom surface 322 can be substantially flat. Alternatively, the bottom surface 322 can be convex or concave. The socket component 304 can have one or more grooves 320 depending on the particular application. In some implementations, the socket component 304 may have just one groove 320. Alternatively, the socket component 304 may have between two and five grooves. In some implementations, the socket component may have more than five grooves. In some implementations, the bearing surface 308 has a surface area that acts against the convex bearing surface that is 70% or less, or 50% or less than a continuous surface with the same curvature (e.g., the surface 208 of the component 204).

Figure 5:
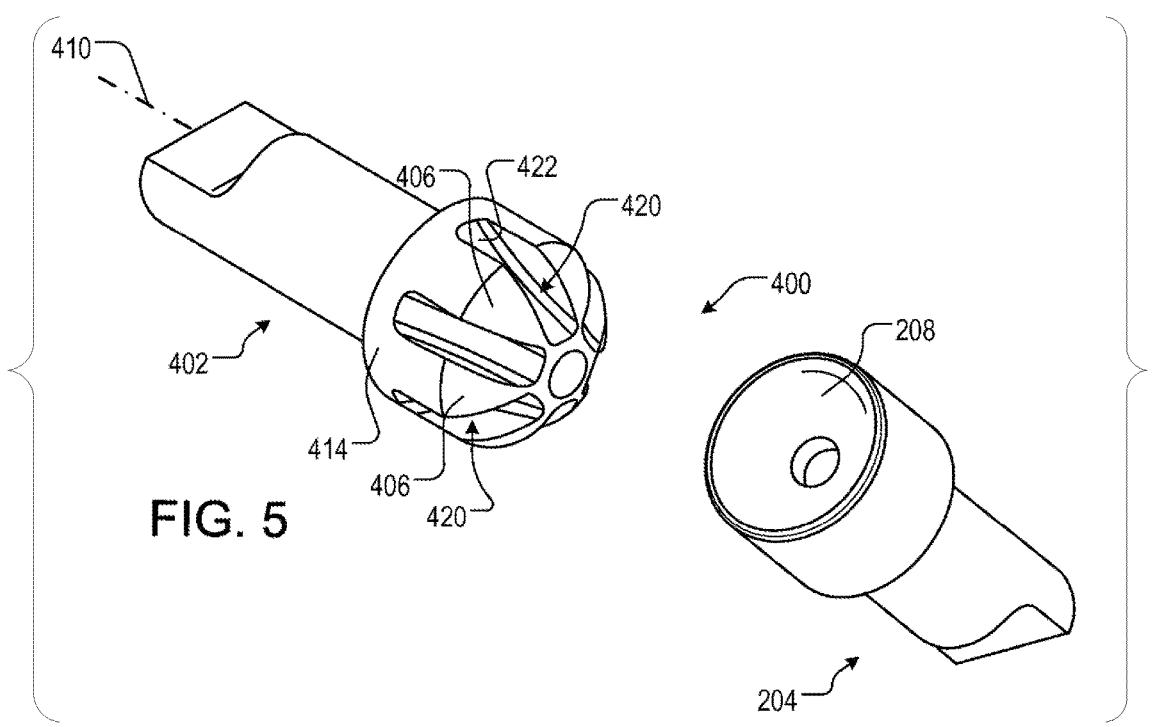

Referring to FIG. 5, a bearing assembly 400 includes the socket component 204 of FIGS. 3A-3C and an alternative ball component 402. Similar to the bearing assembly 300 of FIG. 4, the bearing assembly 400 has a component (e.g., the ball component 402) that defines voids that, among other things, may promote heat dissipation through increased fluid flow and may reduce friction at the bearing interface.

The ball component 402 has a convex bearing surface 406 having the same curvature shown for the bearing surface 206 of the ball component 202. The ball component 402 also has a generally cylindrical outer surface outer surface 414 adjacent the convex bearing surface 206. The ball component 402 defines voids that are in the form of grooves 420 that extend between the bearing surface 406 and the outer surface 414. In contrast to the generally smooth and continuous bearing and outer surfaces 206, 214 shown in FIG. 3B, the bearing surface 406 and the outer surface 414 each define portions of the grooves 420 and are thus discontinuous. As a result, portions of the convex bearing surface 406 are separated by the grooves 420.

The grooves 420 are generally open channels that extend radially outward and rearward with respect to an axis of rotation 410 while traversing the bearing surface 406 and the outer surface 414. Similar to grooves 320 (FIG. 4), the grooves 420 are configured to allow the passage of blood. Each groove 420 can have a bottom surface 422 that faces outward through the open portion of the groove 420. In some implementations, the bottom surface 422 can be substantially flat. Alternatively, the bottom surface 422 can be convex or concave, or may have another curvature.

During pump operation, blood can flow into the groove 420 by entering through an opening defined by the bearing surface 406 and can flow out of the groove 420 by exiting through an opening defined by the outer surface 414. Alternatively, or additionally, blood may enter the groove 420 through the opening in the outer surface 414 while exiting through the opening in the bearing surface 406. The blood flow into the bearing interface can lead to, for example, increased cooling of the bearing assembly 400. Additionally, the grooves 420 can provide a passageway through which any particles that may have formed or become dislodged in the bearing interface may be jettisoned.

In some implementations, a radial depth of the groove 420 can vary along the axial length of the groove 420. The ball component 402 can have one or more grooves 420. In the example illustrated, the ball component 402 defines six grooves that are equally spaced apart about the axis 410. In some implementations, the ball component 402 may have just one groove 420. Alternatively, the ball component 402 may have between two and five grooves. In some implementations, the socket component may have more than five grooves. In some implementations, the bearing surface 406 has a surface area that is 70% or less, or 50% or less than a continuous surface with the same curvature (e.g., the surface 206 of the component 202).

Figure 6:
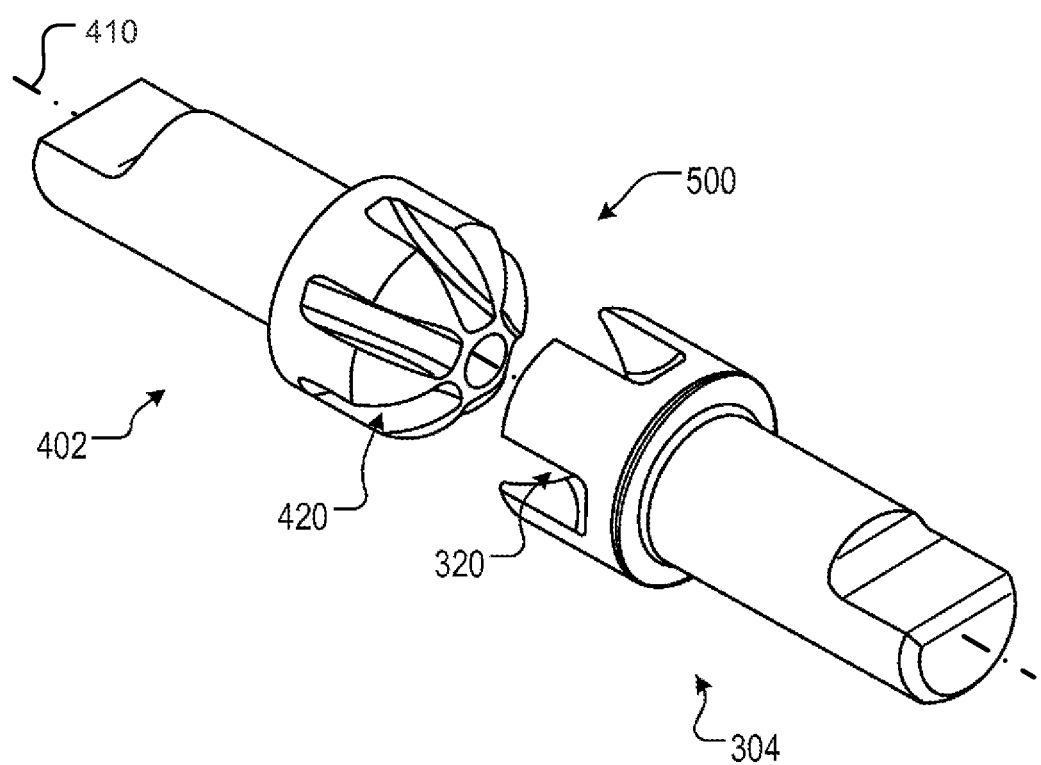

Referring to FIG. 6, an alternative bearing assembly 500 may be formed by combining the ball component 402 defining grooves 420 (FIG. 5) with the socket component 304 defining grooves 320 (FIG. 4). With grooves defined through the bearing surfaces of both components 304, 402, the surface area acting against each other at the interface of the components 304, 402 is further reduced. In addition, blood flow in and through the interface may be increased.

As shown in FIGS. 4-6, grooves may be defined in a bearing component that is held stationary in the blood flow path (e.g., mounted to the housing 110 of the pump 100a), a bearing component that rotates (e.g., carried on the rotor 120), or both bearing components.

Figure 7:
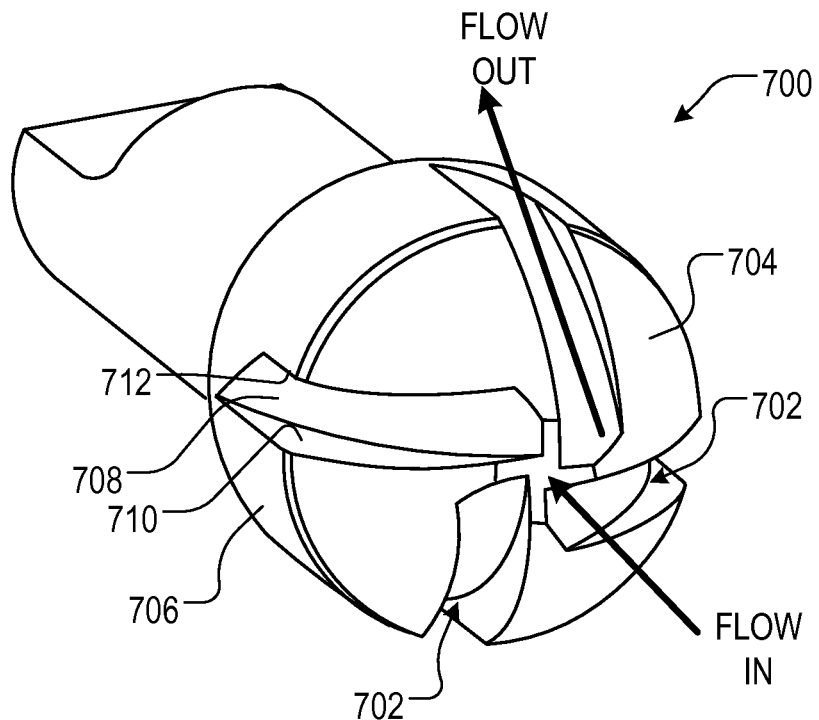

Referring to FIG. 7, a ball component 700 defines flute-like grooves 702. The grooves 702 extend across a convex bearing surface 704 and an outer surface 706. The ball component 700 is configured to be received by a complementary socket component, such as one of the socket components 204, 304 described above. As illustrated, the grooves 702 can be in the form of flutes with knife-like edges that can cut through particles that may become lodged at the bearing interface.

Each groove 702 can include a bottom surface 708 that is tilted with respect to the bearing surface 704 such that a height of a sidewall 710 that runs along one side of the bottom surface 708 may generally be greater than a height of a sidewall 712 that runs along the opposite side. Also as illustrated, the grooves 702 may be offset from a center of the bearing surface 704 such that they are not centered at the axis of rotation. During operation, blood may enter the grooves 702 at a region near the center of the bearing surface 704, flow along a length of the grooves 702, and exit through the outer surface 706. A sharp edge formed, for example, at an intersection of the bearing surface 704 with the sidewall 710 and/or sidewall 712, may help cut or shred through particles as mentioned above. FIG. 7 illustrates four grooves 702, but more or fewer grooves 702 may be used. The sidewalls 710, 710 can be planar and can extend parallel to an axis of rotation of the ball component 700.

Figure 8:
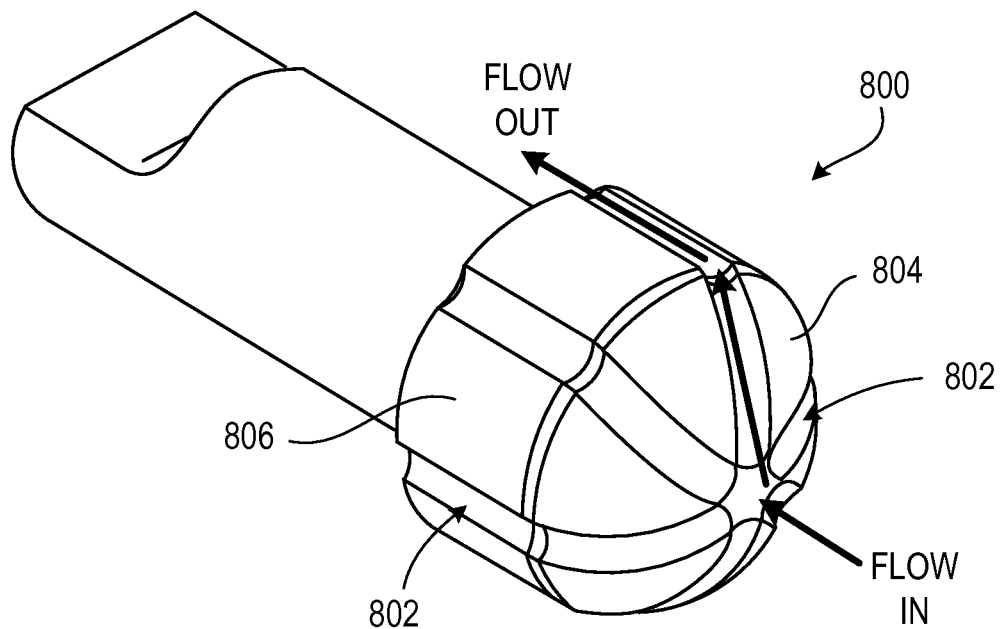

Referring to FIG. 8, a ball component 800 defines flute-like grooves 802 that extend across a convex bearing surface 804 and an outer surface 806. The ball component 800 is configured to be received by a complementary socket component socket component, such as one of the socket components 204, 304 described above. As illustrated, the grooves 802 can be in the form of curved flutes that enhance dispelling of fluid and particles from the bearing interface. Each groove 802 can have a curved path across the bearing surface 804 before extending longitudinally across the outer surface 806, in a direction parallel to the axis of rotation. Alternatively, the grooves 802 may be defined in a linear path. In some implementations, each groove 802 can extend across an entire axial length of the outer surface 806. In some implementations, the depth of each groove 802 into the exterior of the ball component 800 is substantially constant along the entire groove 802. FIG. 8 illustrates six grooves 802, but more or fewer grooves 802 may be used.

In some implementations, as shown in FIGS. 9A, 9B, 10A, and 10B, a socket component of a bearing assembly may define bores or other channels to promote fluid flow through the bearing assembly.

Figure 9A:
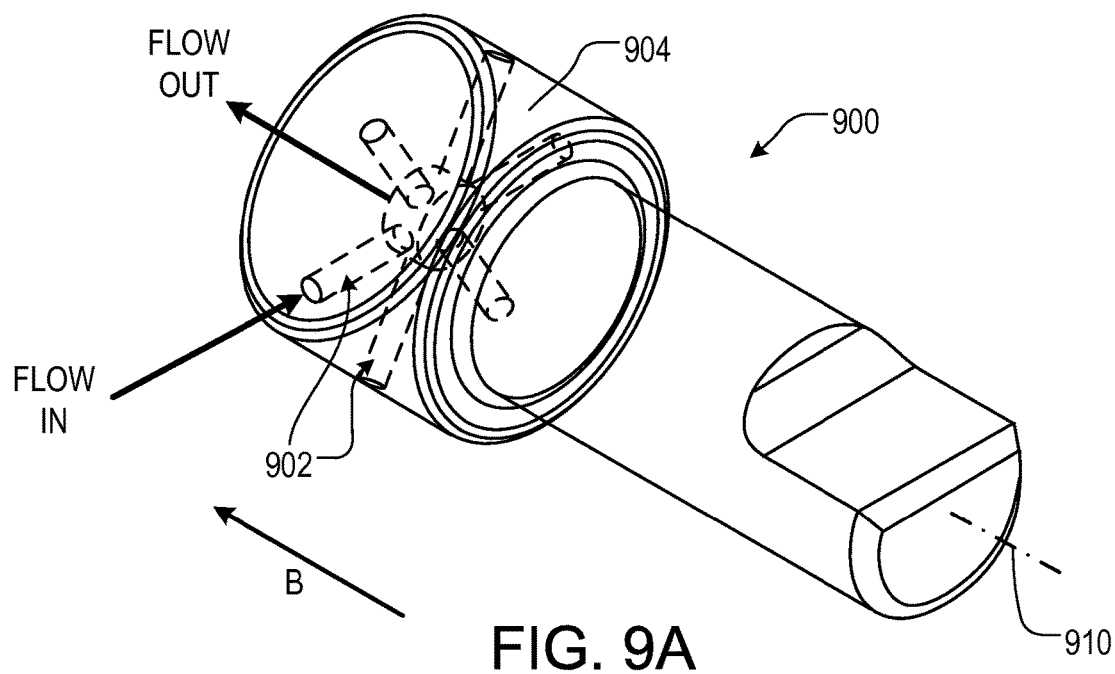
FIGS. 9A and 9B are perspective views of an alternative bearing.
Figure 9B:
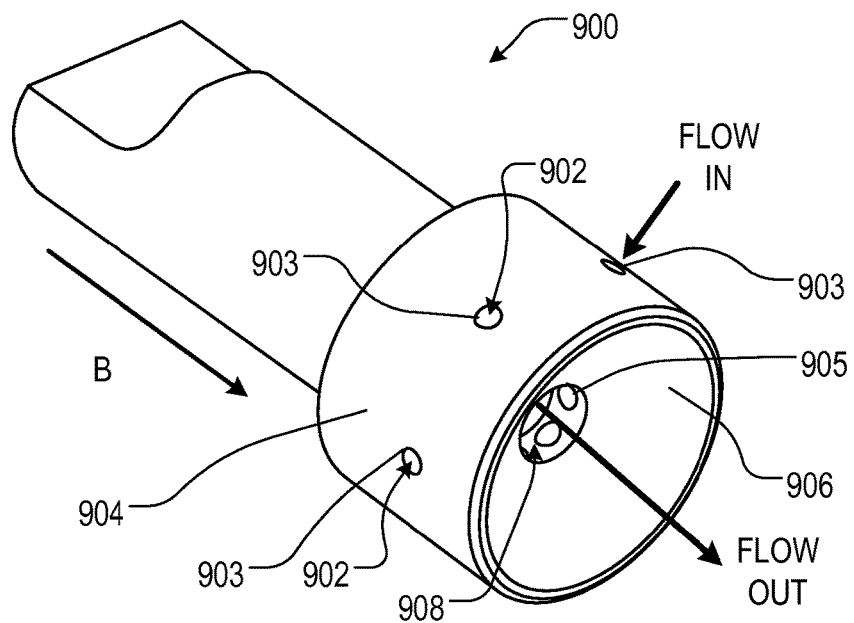

Referring to FIGS. 9A and 9B, a socket component 900 defines a plurality of bores 902 that extend radially from an axis of rotation 910. The bores 902 provide establish fluid communication between the exterior of the socket component 900 and a concave bearing surface 906.

The bores 902 extend through the socket component 900 in a direction that is substantially orthogonal to the axis of rotation 910. For example, the bores 902 begin at an entry opening 903 defined in a cylindrical outer surface 904, and the bores 902 extend inward from toward the axis of rotation 910. The bores 902 extend to an exit opening 905 at a chamber 908 defined in the concave bearing surface 906. In this manner, the bores 902 establish fluid communication from the exterior of the socket component 900 to the interior of the chamber 908. In some implementations, the chamber 908 is a cylindrical recess located at the center of the concave bearing surface 906, which is open to the concave bearing surface 906. In the example, each bore 902 is a passage with a linear trajectory. However, in some implementations, the bores 902 may extend along a curved trajectory.

During operation, blood typically flows in a direction indicated by arrow B. As blood flows past the socket component 900, some blood enters the bores 902 through the entry openings 903 in the outer surface 904 and exits through the exit openings 905 into the cylindrical chamber 908. Blood entering the chamber 908 can flow into and through a gap between the concave bearing surface 906 and, for example, a complementary convex bearing surface of a ball component. The flow through the bores 902 may enhance heat dissipation to cool the socket component 900. The example shown in FIGS. 9A and 9B includes six bores 902. However, implementations may define more or fewer bores 902. In some implementations, one, two, three, four, five, or more bores are used.

The bores 902 may have a generally circular cross-section, as illustrated. Alternatively, the bores 902 may have non-circular cross-sections, for example, elliptical or rectangular cross-sections, to name a few. In some implementations, the bores 902 may have a non-uniform cross-section. That is, the shape or size of the cross-section may vary along a length of each bore 902. For example, the bores 902 may be frustoconical in shape.

Figure 10A:
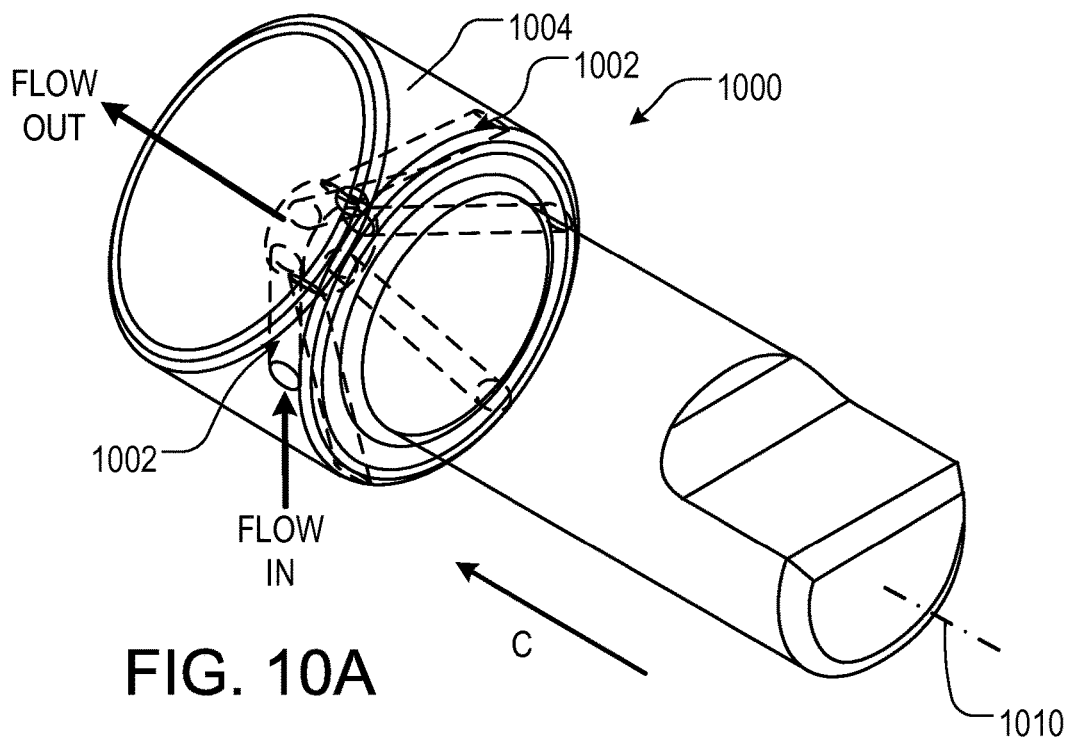
FIGS. 10A and 10B are perspective views of an alternative bearing.
Figure 10B:
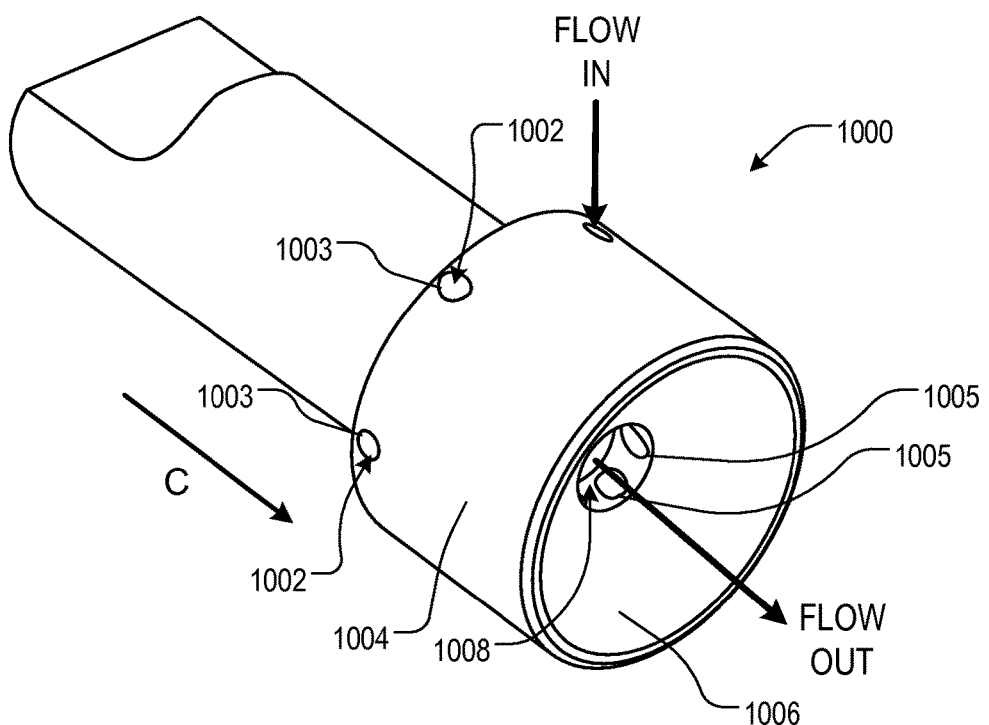

Referring to FIGS. 10A and 10B, a socket component 1000 defines bores 1002 that establish fluid communication between an outer surface 1004 and a convex bearing surface 1006. The bores 1002 are angled with respect to an axis of rotation 1010, for example, oriented at a diagonal to the axis 1010. For example, the bores 1002 may extend at an angle of between 30 degrees to 80 degrees, or approximately 45 degrees with respect to the axis 1010.

The socket component 1000 defines an entry opening 1001 of each bore 1002 in the outer surface 1004 and defines an exit opening 1005 of each bore 1002 at a cylindrical chamber 1008 in communication with the concave bearing surface 1006. Blood flows through the pump in the direction of arrow C. The bores 1002 are angled or swept backward, so that the entry opening 1001 is located upstream of the exit opening 1005. During operation, blood will typically flow in a direction indicated by arrow C and may pass through the bores 1002, exiting into the cylindrical chamber 1008. In some implementations, relative rotation of bearing components may further help draw blood through the bores 1002 and into the bearing interface, which may promote heat dissipation to cool the socket component 1000.

FIGS. 10A and 10B illustrate six bores 1002, but more or fewer bores 1002 may be used. The bores 1002 may have a generally circular cross-section. Alternatively, the bores 1002 may have non-circular cross-sections, for example, elliptical or rectangular cross sections, to name a few. In some implementations, the bores 1002 may have a non-uniform cross-section. That is, the shape or size of the cross-section may vary along a length of each bore 1002. For example, the bores 1002 may be frustoconical in shape.

A number of embodiments of the invention have been described. Nevertheless, it will be understood that various modifications may be made without departing from the spirit and scope of the invention. For example, grooves formed in one or both of the ball and socket components of a bearing assembly may be straight, zigzag, spiral, or meandering in shape. Similarly, one or more components of a bearing assembly may include grooves along a bearing surface and may include one or more bores or internal passages between an outer surface and a bearing surface. Accordingly, other embodiments are within the scope of the following claims.

What is claimed is:

1. A method of supporting an impeller in a blood pump, the method comprising,
   supporting the impeller within a blood flow channel of the blood pump via a bearing, the bearing having a first bearing surface and, a second bearing surface that opposes the first bearing surface, wherein the impeller is positionable within the blood flow channel so that the first bearing surface and the second bearing surface are separated by an interface region;
   passing a flow of blood through the blood flow channel so that blood at least partially surrounds the first bearing surface and the second bearing surface;
   passing blood through the interface region by rotating the impeller within the blood flow channel; and
   flowing blood along at least one void in at least one of the first bearing surface and the second bearing surface.

2. The method of claim 1, comprising:
   receiving the flow of blood from a ventricle of the heart; and
   supplying the flow of blood to an artery.

3. The method of claim 1, wherein flowing blood along the at least one void in at least one of the first bearing surface and the second bearing surface comprises:
   flowing blood along at least one surface groove in at least one of the first bearing surface and the second bearing surface; and
   distributing blood from the blood flowing along the at least one surface groove into a surrounding portion of at least one of the interface region adjacent to the at least one surface groove.

4. The method of claim 1, wherein flowing blood along the at least one void comprises:
   flowing blood along a first plurality of surface grooves in the first bearing surface;
   distributing blood from the blood flowing along the first plurality of surface grooves into surrounding portions of the interface region adjacent to the first plurality of surface grooves; and
   flowing blood from the interface region along a second plurality of surface grooves in the second bearing surface.

5. The method of claim 1, wherein flowing blood along the at least one void comprises:
   flowing blood through at least one fluid channel through at least one of the first bearing surface and second bearing surface; and
   distributing blood from the blood flowing through the at least one fluid channel to the interface region.

6. The method of claim 1, wherein the flow of blood passing through the blood flow channel flows over at least one of the first bearing surface and the second bearing surface, so as to prevent a buildup of particulates on the at least one of the first bearing surface and the second bearing surface.

7. The method of claim 1, comprising dissipating heat from the interface region via the flow of blood passing through the blood flow channel.

8. The method of claim 1, comprising:
separating the first bearing surface and the second bearing surface via a layer of blood.

9. The method of claim 1, wherein the flowing blood along the at least one void comprises:
directing at least a portion of the flow of blood along a helical path in the blood flow channel by flowing at least a portion of the flow of blood through at least one surface groove in at least one of the first bearing surface and the second bearing surface; the at least one surface groove being offset relative to a center of at least one of the first bearing surface and second bearing surface, such that the at least one surface groove lies substantially along a plane offset from and parallel to a rotational axis of at least one of the first bearing surface and the bearing surface.

10. The method of claim 9, wherein directing the at least a portion of the flow of blood along the helical path in the blood flow channel comprises:
flowing blood from a central region of the first interface region into the at least one surface groove, along the at least one surface groove, and out from the at least one surface groove at a side of the at least one of the first bearing surface and the second bearing surface.

11. The method of claim 9, wherein directing the at least a portion of the flow of blood along the helical path in the blood flow channel comprises:
flowing the at least a portion of the flow of blood through at least one curved surface groove in at least one of the first bearing surface and the second bearing surface, the at least one surface groove comprising a helical path along a working surface of one or more of the first bearing surface and the second bearing surface.

12. The method of claim 9, wherein at least one of:
the second biocompatible material is the same as the first biocompatible material; and
the third biocompatible material is the same as the second biocompatible material.

13. The method of claim 1, wherein flowing blood along the at least one void comprises:
drawing blood from the flow of blood through at least one bore in a side surface of one or more of the first bearing surface and the second bearing surface, and into the interface region; and
distributing blood from the blood flowing through the at least one bore to the interface region.

14. A method of manufacturing a blood pump bearing, the method comprising:
forming a first element of the blood pump bearing from a first biocompatible material by shaping a first working surface in either of a convex or a concave shape;
forming a second element of the blood pump bearing from a second biocompatible material by shaping a second working surface configured to receive the first working surface in an axially rotatable configuration, the second working surface being sized relative to the first working surface sufficient to accommodate a layer of blood between the first and second working surfaces and formed in either a concave or a convex shape; and
forming a plurality of voids in one or more of the first working surface and the second working surface.

15. The method of claim 14, wherein forming the plurality of voids comprises:
removing a portion of material from one or more of the first working surface and the second working surface such that the removed portion defines a plurality of negative surface features in the one or more working surfaces.

16. The method of claim 15, wherein removing the portion of material comprises cutting grooves in the one or more of the first working surface and second working surface via at least a milling operation.

17. The method of claim 15, wherein removing the portion of material comprises forming bores from a side surface of one or more of the first blood pump bearing element and the second blood pump bearing element to one or more of the first working surface and second working surface via at least a drilling operation.

18. The method of claim 14, wherein forming the plurality of voids comprises forming one or more of the first and second blood pump bearing elements via a molding step with a mold having inclusions defining the plurality of voids.

19. The method of claim 14, wherein:
forming the first blood pump bearing element comprises shaping a convex surface of the first biocompatible material; and
forming the second blood pump bearing element comprises shaping a concave surface of the second biocompatible material, wherein the convex surface is sized to rest in the concave surface in a ball-and-socket arrangement.

20. The method of claim 14, wherein the second biocompatible material is the same as the first biocompatible material.

21. A method of manufacturing blood pump bearings, the method comprising:
forming a first blood pump bearing element from a first biocompatible material by shaping a first working surface in either of a convex or a concave shape;
additively coating the first working surface with a second biocompatible material so as to form one or more surface grooves on the first blood pump bearing element; and
forming a second blood pump bearing element from a third biocompatible material by shaping a second working surface configured to receive the first working surface in an axially rotatable configuration, the second working surface being sized relative to the first working surface sufficient to accommodate a layer of blood between the first and second working surfaces and formed in either a concave or a convex shape.

22. The method of claim 21, wherein additively coating comprises depositing material via a vapor deposition process.

23. A method of manufacturing blood pump bearings, the method comprising:
forming a first component of the blood pump bearings having a base surface and an outer surface adjacent to the base surface;
additively coating first portions of the base surface with a biocompatible material, such that the first portions have a first thickness and form a first working surface, and such that second portions have a second thickness and form grooves in the working surface; and
forming a second component of the blood pump bearings by shaping a second working surface configured to receive the first working surface in an axially rotatable configuration, the second working surface being sized relative to the first working surface sufficient to accommodate a layer of blood between the first and second working surfaces and formed in either a concave or a convex shape.

24. The method of claim 23, wherein additively coating the first portions of the base surface with the biocompatible material comprises depositing material via a vapor deposition process.

* * * * *